(12) United States Patent
Safai et al.

(10) Patent No.: US 12,035,663 B2
(45) Date of Patent: Jul. 16, 2024

(54) IRRIGATION MANAGEMENT SYSTEM

(71) Applicant: M8 Systems, Inc., San Juan Capistrano, CA (US)

(72) Inventors: Max Safai, San Juan Capistrano, CA (US); Herbert Lawson Fisher, Portola Valley, CA (US)

(73) Assignee: M8 Systems, Inc., San Juan Capistrano, CA (US)

( * ) Notice: Subject to any disclaimer, the term of this patent is extended or adjusted under 35 U.S.C. 154(b) by 281 days.

(21) Appl. No.: 17/720,135

(22) Filed: Apr. 13, 2022

(65) Prior Publication Data

US 2022/0400631 A1 Dec. 22, 2022

Related U.S. Application Data

(60) Provisional application No. 63/211,395, filed on Jun. 16, 2021.

(51) Int. Cl.
*A01G 25/16* (2006.01)
*F15B 15/20* (2006.01)
*F16K 31/124* (2006.01)
*F16K 31/53* (2006.01)
(Continued)

(52) U.S. Cl.
CPC .............. *A01G 25/16* (2013.01); *F15B 15/20* (2013.01); *F16K 31/1245* (2013.01); *F16K 31/535* (2013.01); *G01N 1/2035* (2013.01); *G01N 2001/205* (2013.01); *G01N 33/18* (2013.01)

(58) Field of Classification Search
CPC ...... G01N 33/18; G01N 1/2035; A01G 25/16; F15B 15/20; F16K 31/535; F16K 31/1245
See application file for complete search history.

(56) References Cited

U.S. PATENT DOCUMENTS

| 7,720,574 | B1 | 5/2010 | Roys |
| 10,039,240 | B2 | 8/2018 | Darnold |
| 10,271,474 | B1 | 4/2019 | Miller et al. |

(Continued)

FOREIGN PATENT DOCUMENTS

RU 2467560 C2 11/2012

OTHER PUBLICATIONS

Office Action, U.S. Appl. No. 17/841,943, mailed Jul. 31, 2023.

*Primary Examiner* — Jamel E Williams
(74) *Attorney, Agent, or Firm* — Master Key IP, LLP; Justin G. Sanders

(57) ABSTRACT

An irrigation management system is disclosed and positionable in-line with an irrigation pipe for monitoring and controlling a flow of fluid therethrough. In at least one embodiment, the system provides an inlet pipe and an opposing outlet pipe in serial fluid communication with the irrigation pipe. At least one fluid control valve is in serial fluid communication between the inlet pipe and outlet pipe for selectively controlling the flow of fluid therebetween. The fluid control valve provides a main valve and a hydraulic actuator for selectively moving the main valve between open and closed positions. The hydraulic actuator is also in serial fluid communication between a pair of actuator valves for moving the hydraulic actuator between open and closed positions. The system also provides at least one sample collection tank configured for temporarily storing a volume of fluid diverted from the irrigation pipe in order to be tested.

20 Claims, 8 Drawing Sheets

(51) Int. Cl.
    *G01N 1/20*         (2006.01)
    *G01N 33/18*       (2006.01)

(56) References Cited

U.S. PATENT DOCUMENTS

| | | |
|---|---|---|
| 10,561,078 B2 | 2/2020 | Darnold |
| 10,788,438 B2 | 9/2020 | Nemecek et al. |
| 2004/0217189 A1 * | 11/2004 | Regli .................. A01G 25/167 239/69 |
| 2006/0196543 A1 | 9/2006 | Hunt et al. |
| 2011/0308618 A1 | 12/2011 | Lorenz |
| 2012/0228117 A1 | 9/2012 | Panunzio |
| 2020/0093077 A1 | 3/2020 | Darnold |

* cited by examiner

IRRIGATION MANAGEMENT SYSTEM

RELATED APPLICATIONS

This application claims priority and is entitled to the filing date of U.S. provisional application Ser. No. 63/211,395, filed on Jun. 16, 2021. The contents of the aforementioned application are incorporated herein by reference.

BACKGROUND

The subject of this provisional patent application relates generally to irrigation systems, and more particularly to an irrigation management system that provides cost-effective, less power consuming fluid control valves and cost-effective in-line water quality testing capabilities.

Applicant(s) hereby incorporate herein by reference any and all patents and published patent applications cited or referred to in this application.

By way of background, water is becoming a scarce resource worldwide, which has had a significant impact on food production. According to research, agriculture accounts for roughly 70 percent of global water withdrawals. Some areas of the United States use up to 90 percent of available water for agricultural purposes. As water resources become less dependable or available in many areas, the efficient use of water is an important topic for the agricultural industry—especially since water prices have continued to rise for growers. Thus, the reliability of valves for controlling water flow in such irrigation systems—so as to deliver a correct volume of water without delivering any excess—is becoming increasingly more important. Current irrigation valves are typically either operated manually or are motor driven. While motor driven valves allow an irrigation system to be operated automatically and/or remotely, they must also be powered by a sufficient amount of electricity (typically requiring large batteries, solar panels, or both) which, in turn, increases overall operational costs for the irrigation system. Thus, there remains a need for a reliable irrigation valve that is capable of being operated automatically and remotely, without prohibitively increasing operational costs for the irrigation system.

Another common practice in irrigation systems is to periodically monitor the quality of the water moving therethrough in order to maximize crop yields. Water analyses can only be as accurate as the sample taken. Given that irrigation water is typically delivered at high pressures (usually 100 psi to 150 psi or higher), it can be difficult if not impossible to conduct proper in-line testing of the water within the irrigation pipes—at least not without the use of specialized or expensive sensors. Instead, most traditional water quality sensors are designed to test ambient pressure water. Thus, there also remains a need for a water quality testing system that is capable of facilitating in-line testing of water within an irrigation pipe without prohibitively increasing operational costs for the irrigation system.

Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing an irrigation management system positionable in-line with an irrigation pipe for monitoring and controlling a flow of fluid therethrough. In at least one embodiment, the system provides an inlet pipe and an opposing outlet pipe in serial fluid communication with the irrigation pipe. At least one fluid control valve is in serial fluid communication between the inlet pipe and outlet pipe for selectively controlling the flow of fluid therebetween. The fluid control valve provides a main valve and a hydraulic actuator in mechanical communication with the main valve for selectively moving the main valve between open and closed positions. The hydraulic actuator is also in serial fluid communication between a pair of actuator valves configured for moving the hydraulic actuator between open and closed positions. The system also provides at least one sample collection tank configured for temporarily storing a volume of fluid diverted from the irrigation pipe in order to be tested. The sample tank provides a diverter valve positioned in fluid communication between the sample collection tank and at least one of the inlet pipe and outlet pipe, through which fluid from the irrigation pipe may selectively flow into the sample collection tank. At least one drain valve is positioned and configured for draining any stored fluid from the sample collection tank. At least one fluid sensor is positioned within the sample collection tank and configured for monitoring the fluid flowing through the irrigation pipe. The system also provides at least one controller in communication with the at least one fluid sensor and fluid control valve, the at least one controller configured for receiving data collected by the at least one fluid sensor and selectively actuating the at least one fluid control valve Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
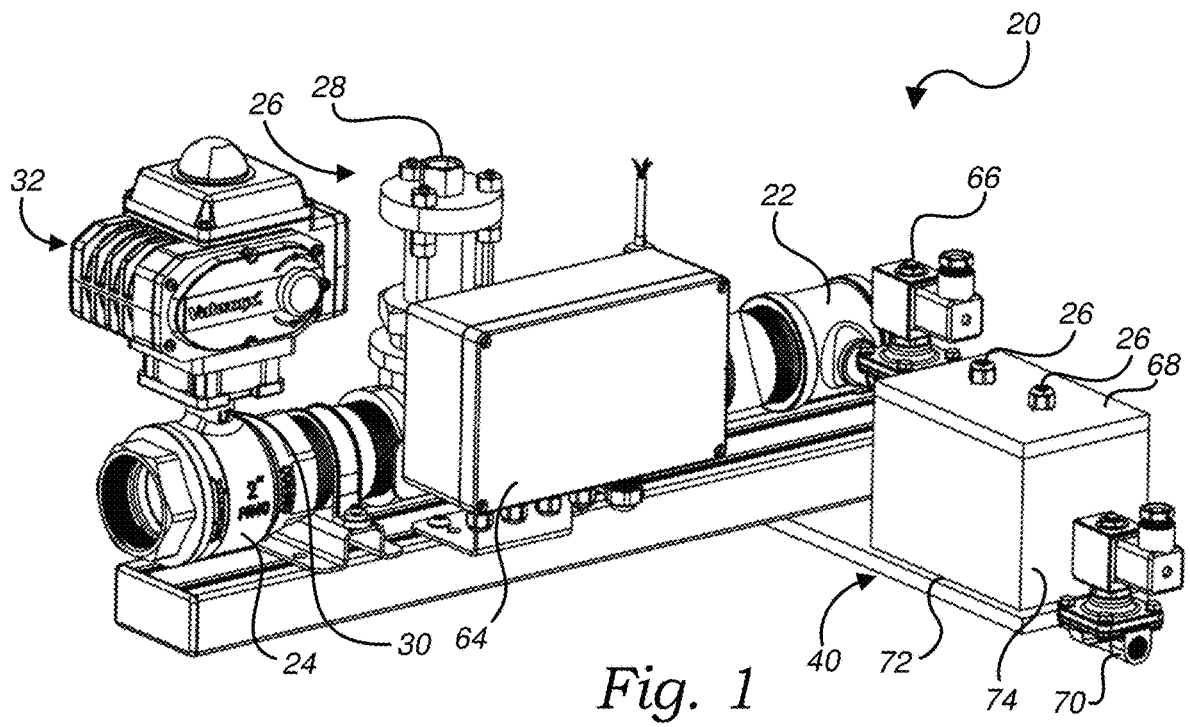
FIG. 1 is a perspective view of an exemplary irrigation management system, in accordance with at least one embodiment.

Turning now to FIG. 1, there is shown a perspective view of an exemplary irrigation management system 20, in accordance with at least one embodiment, positionable in-line with an irrigation pipe (not shown) for monitoring and controlling a flow of fluid therethrough.

In at least one embodiment, the system 20 provides an inlet pipe 22 and an opposing outlet pipe 24, with each of the inlet and outlet pipes 22 and 24 being in fluid communication with the irrigation pipe. Accordingly, fluid flows from the irrigation pipe into the inlet pipe 22, through the system 20, and subsequently exits via the outlet pipe 24 where it then continues on through the remainder of the irrigation pipe. Additionally, in at least one embodiment, the system 20 provides an at least one fluid sensor 26 positioned and configured for monitoring the fluid flowing through the irrigation pipe. In at least one such embodiment, the at least one fluid sensor 26 is at least one of a fluid flow sensor 28 and a fluid pressure sensor 30. In still further such embodiments, the at least one fluid sensor 26 may be any other type of sensor, now known or later developed, capable of allowing the system 20 to carry out the functionality herein described. For example, in at least one such further embodiment, the at least one fluid sensor 26 is a chemical analysis sensor (such as a fluid temperature sensor, a conductivity sensor, or a turbidity sensor, for example) capable of analyzing the fluid for characteristics such as salinity, suspended solids, and dissolved mineral content. In at least one embodiment, as discussed further below, the system 20 also provides an at least one supplemental sensor (not shown) positioned and configured for gathering additional data related to the fluid flowing through the irrigation pipe, as discussed further below. In at least one such embodiment, the at least one supplemental sensor is at least one of a fluid level sensor, a luminosity sensor, a humidity sensor, an air temperature sensor, a rain sensor, and a soil moisture sensor. In at least one further embodiment, where the irrigation pipe is in fluid communication with an at least one fluid pump, the at least one supplemental sensor includes an electrical current sensor and/or voltage sensor positioned and configured for monitoring the electrical usage of the pump. In at least one still further embodiment, the at least one supplemental sensor is a meter reading device positioned and configured for capturing images of a display of an existing meter (such as a fluid meter display, for example), and converting the captured display images into numerical data (using image-to-text conversion methods) for subsequent processing by the system 20. In still further embodiments, the at least one supplemental sensor may be any other type of sensor, now known or later developed, capable of allowing the system 20 to carry out the functionality herein described.

With continued reference to FIG. 1, in at least one embodiment, the system 20 also provides an at least one fluid control valve 32 in fluid communication with each of the inlet pipe 22 and outlet pipe 24 and positioned in-line therebetween. The at least one fluid control valve 32 is configured for being selectively actuated for controlling the flow of fluid through the system 20 and, in turn, the irrigation pipe as discussed further below. It should be noted that while the fluid control valve 32 is discussed in the context of the irrigation management system 20, the fluid control valve 32 should not be interpreted as being so limited. Instead, the fluid control valve 32 may be utilized in virtually any pipe system where there is a desire to control the flow of a fluid therethrough (not just water).

Figure 2:
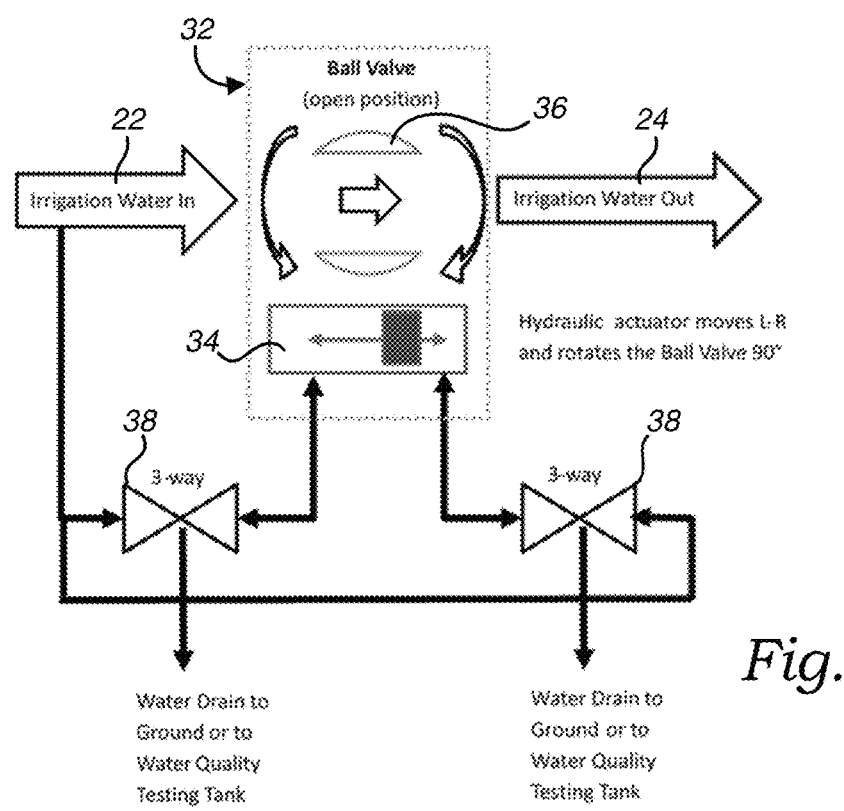
FIG. 2 is a diagrammatic view of an exemplary fluid control valve, in accordance with at least one embodiment.

In at least one embodiment, the at least one fluid control valve 32 is selectively actuated using stored energy in the high-pressure irrigation pipe. In a bit more detail, in at least one embodiment, as illustrated in FIG. 2, the at least one fluid control valve 32 provides a hydraulic actuator 34 in mechanical communication with a main valve 36—such as a ball valve or butterfly valve, for example—for selectively moving the main valve 36 between an open position (whereby fluid is allowed to flow therethrough) and a closed position (whereby fluid is prevented from flowing therethrough). In at least one embodiment, the at least one fluid control valve 32 provides a valve sensor (not shown)—such as an encoder, for example—positioned and configured for determining whether the main valve 36 is in the open position or the closed position (or partially open position, in at least one embodiment) at any given time. Additionally, in at least one embodiment, the at least one fluid control valve 32 provides a pair of actuator valves 38—such as solenoid valves, for example—in fluid communication with the hydraulic actuator 34 and configured for moving the hydraulic actuator 34 between an open position (whereby the hydraulic actuator 34 moves the main valve 36 into the open position) and a closed position (whereby the hydraulic actuator 34 moves the main valve 36 into the closed position). It should be noted that moving the hydraulic actuator 34 between the open and closed positions also includes any position between the open and closed positions (referred to herein as a "partially open" position). In at least one embodiment, the actuator valves 38 are in parallel fluid communication with the inlet pipe 22, such that the fluid flowing through the irrigation pipe also flows through the actuator valves 38 and, in turn, the hydraulic actuator 34 (in at least one embodiment). In other words, in such embodiments, the hydraulic actuator 34 is selectively moved between the open and closed position using the fluid flowing through the irrigation pipe. Additionally, in at least one embodiment, a first one of the actuator valves 38 is positioned and configured for moving the hydraulic actuator 34 into the open position, while a second one of the actuator valves 38 is positioned and configured for moving the hydraulic actuator 34 into the closed position. In at least one embodiment, each of the actuator valves 38 is a relatively small, low power 3-way solenoid valve, which allows for a slow, controlled movement of the hydraulic actuator 34 (and, in turn, the main valve 36) between the open and closed positions. The slow movement is actually advantageous as it reduces stress on the irrigation pipe from any water hammer. Furthermore, such a small 3-way solenoid valve can be driven with less than 6 watts of electricity compared to the 60 watts required by a traditional motor driven ball valve. Such a configuration also eliminates the need for a latching solenoid because the main valve 36 will naturally remain in position from its internal friction. As a still further benefit of the 3-way solenoid valves, once the hydraulic actuator 34 is moved into the desired position (i.e., open or closed) using a volume of the fluid, the volume of fluid can be drained to the ground so that the hydraulic actuator 34 can be subsequently moved into the opposite position (i.e., open to closed, or closed to open) when needed. Given that the volume of fluid is the same fluid moving through the irrigation pipe, there is no issue draining the volume of fluid to the ground. In at least one alternate embodiment, as discussed further below, rather than the used volume of fluid being drained to the ground, it may instead be drained into an at least one sample collection tank 40 for subsequent fluid quality testing. However, in further embodiments, any other valve—now known or later developed—capable of moving the hydraulic actuator 34 between the open and closed positions may be substituted.

Figure 3:
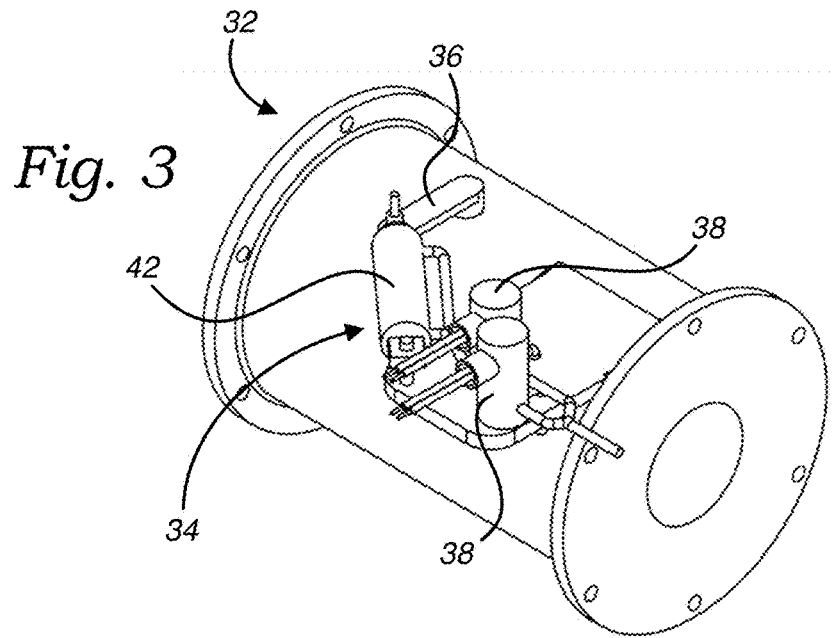
FIG. 3 is a perspective view of an exemplary fluid control valve in an open position, in accordance with at least one embodiment.
Figure 4:
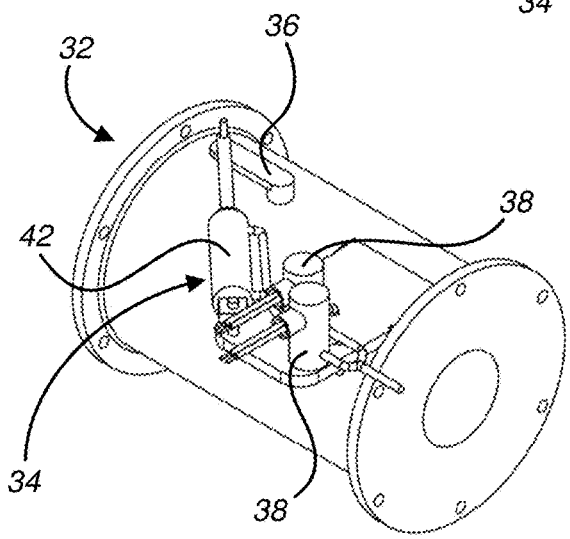
FIG. 4 is a perspective view of the fluid control valve of FIG. 3 in a closed position, in accordance with at least one embodiment.
Figure 5:
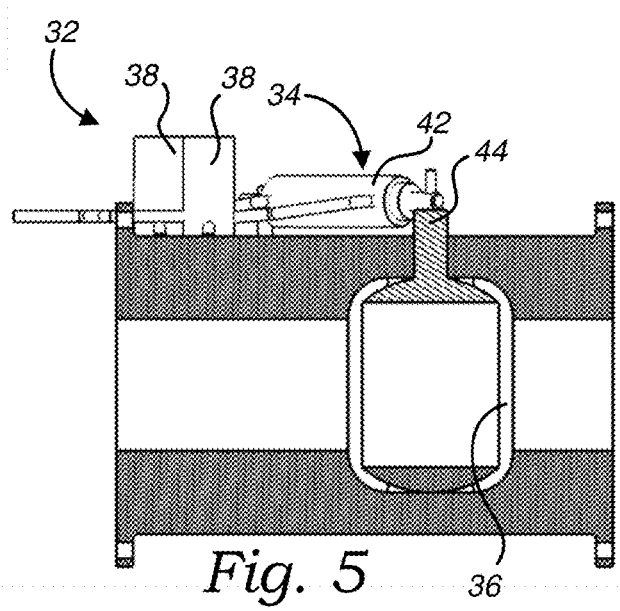
FIG. 5 is a cross-sectional view of the fluid control valve of FIG. 4.

In at least one embodiment, as illustrated in FIGS. 3-5, the hydraulic actuator 34 is a hydraulic cylinder 42 in mechanical communication with an actuation arm 44 provided by the main valve 36. Thus, in such embodiments, as the hydraulic actuator 34 is moved into the open position, the hydraulic cylinder 42 causes the actuation arm 44 to pivot which, in turn, rotates the main valve 36 into the open position; and as the hydraulic actuator 34 is moved into the closed position, the hydraulic cylinder 42 causes the actuation arm 44 to pivot which, in turn, rotates the main valve 36 back into the closed position. In at least one embodiment, the hydraulic cylinder 42 may have any size diameter (dependent upon the size of the main valve 36 to be actuated) without having to change the size of the actuator valves 38—thus, not increasing the drive power needed. In other words, in at least one embodiment, the same actuator valves 38 are capable of actuating any size main valve 36, so long as an appropriately sized hydraulic cylinder 42 is utilized. In at least one embodiment, where the fluid flowing through the irrigation pipe is water or any other fluid that would tend to wash away the lubricants in the hydraulic cylinder 42, the hydraulic cylinder 42 provides a self-lubricating dry seal (such as polytetrafluoroethylene, for example) for the seal between the piston and cylinder. In at least one such embodiment, the self-lubricating dry seal may be a common spring or O-ring backed seal constructed out of, or otherwise coated with, a self-lubricating material.

Figure 6:
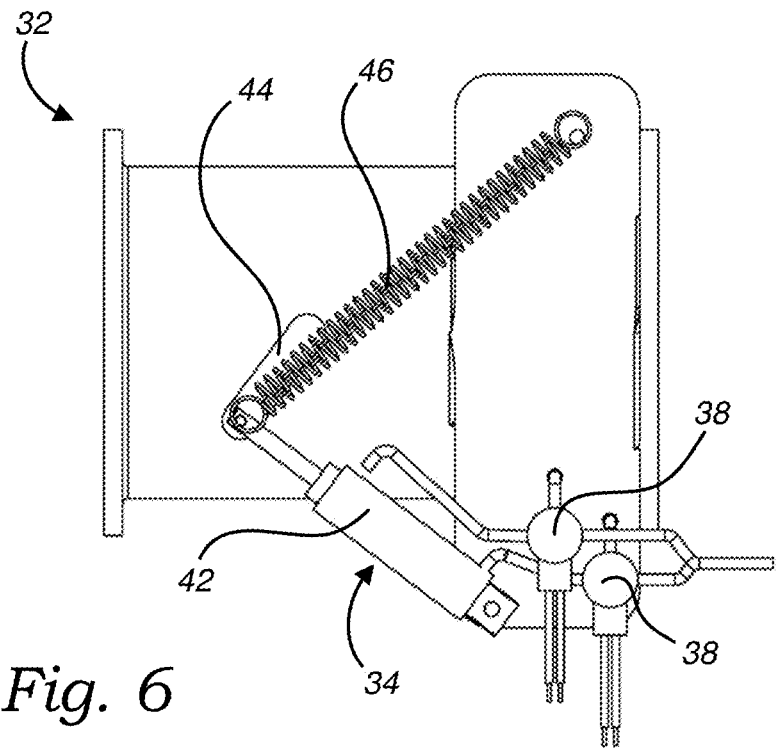
FIG. 6 is a top plan view of a further exemplary fluid control valve, in accordance with at least one embodiment.

In at least one embodiment, as illustrated in FIG. 6, the at least one fluid control valve 32 provides a retention spring 46 engaged with the actuation arm 44 and configured for increasing the force necessary for the hydraulic actuator 34 to move the main valve 36 out of each of the open and closed positions. Thus, in such embodiments, the retention spring 46 effectively turns the main valve 36 into a bi-stable main valve 36.

Figure 7:
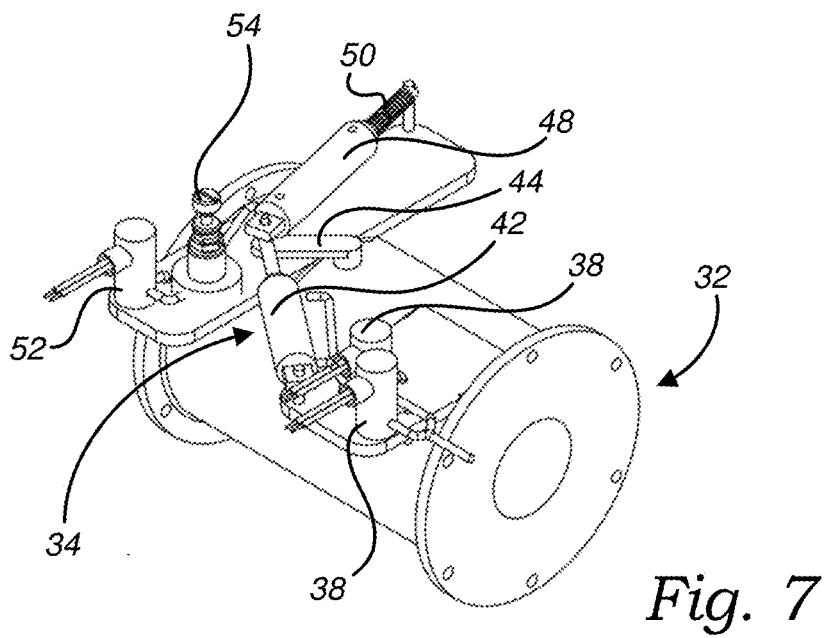
FIG. 7 is a perspective view of a still further exemplary fluid control valve in a partially open position, in accordance with at least one embodiment.
Figure 8:
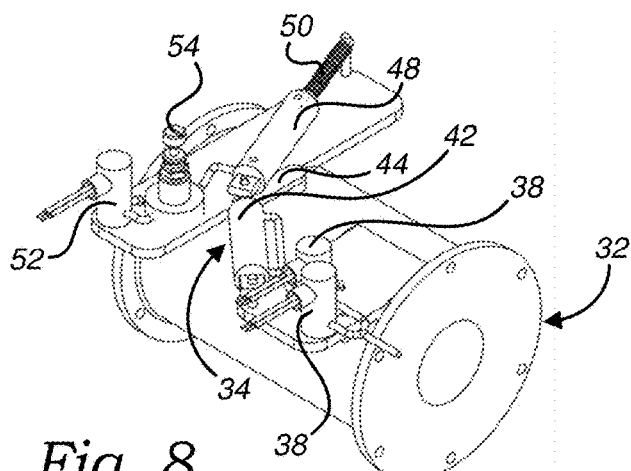
FIG. 8 is a perspective view of the fluid control valve of FIG. 7 in a fully open position, in accordance with at least one embodiment.
Figure 9:
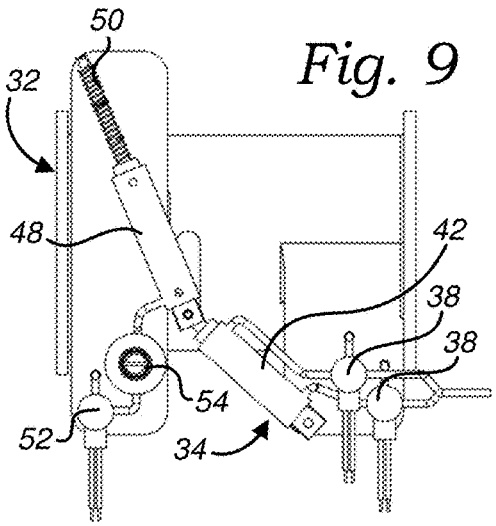
FIG. 9 is a top plan view of the fluid control valve of FIG. 8.
Figure 13:
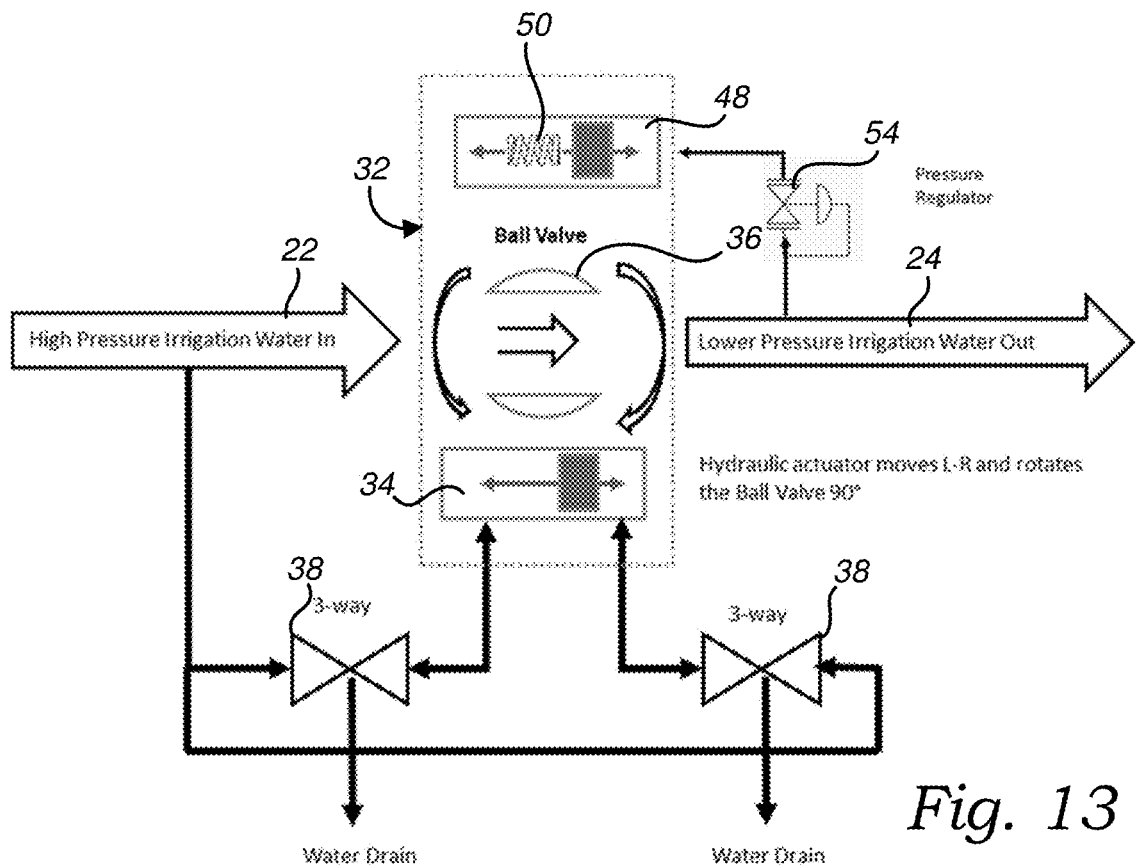
FIGS. 13-15 are diagrammatic views of still further exemplary fluid control valves, in accordance with at least one embodiment.
Figure 14:
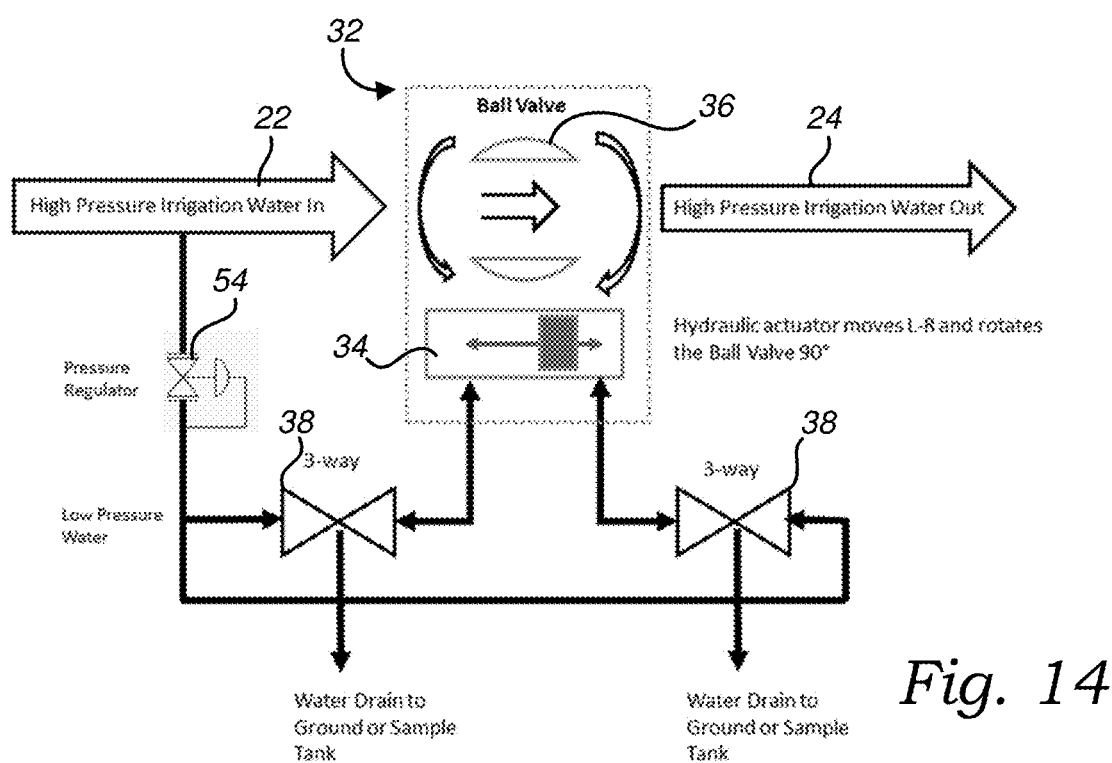
Figure 15:
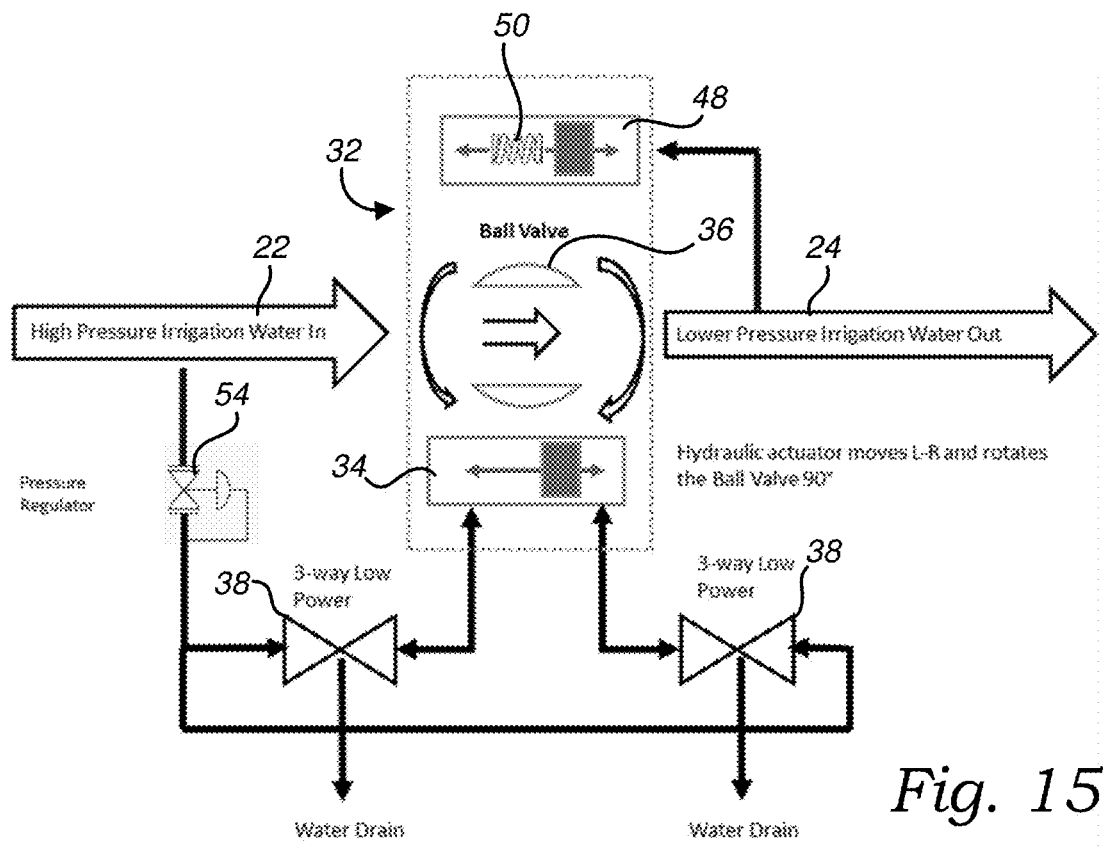

In at least one embodiment, as illustrated in FIGS. 7-9, the at least one fluid control valve 32 provides a hydraulic return actuator 48 in mechanical communication with the main valve 36 for moving the main valve 36 into the closed position (or, alternatively, partially closing the main valve 36) upon the fluid pressure within the system 20 exceeding a pre-defined threshold, thereby better protecting the irrigation pipe from sudden pressure spikes or constant pressure that is greater than the downstream irrigation pipe/system can tolerate. In at least one such embodiment, the hydraulic return actuator 48 is a hydraulic cylinder 42, similar to the hydraulic actuator 34 discussed in detail above. In at least one such embodiment, the hydraulic return actuator 48 has a diameter that is relatively smaller than the diameter of the hydraulic actuator 34, thereby allowing the hydraulic return actuator 48 to be back driven by the hydraulic actuator 34. In at least one embodiment, the pre-defined threshold for the fluid pressure is set by a force adjustable spring 50 positioned on the hydraulic return actuator 48, with the spring 50 configured for biasing the main valve 36 into the open position. Thus, upon the fluid pressure exceeding the pre-defined threshold, the force of the spring 50 is overcome and the main valve 36 is moved into the closed position (or at least a partially closed position). In at least one such embodiment, the at least one fluid control valve 32 further provides a latching valve 52 (such as a 3-way latching solenoid valve, for example) positioned and configured for maintaining the main valve 36 in the closed position after the main valve 36 has been moved into the closed position by the hydraulic return actuator 48—thereby eliminating the need for the second one of the actuator valves 38 to be energized for moving the main valve 36 into the closed position. The latching valve 52 is in parallel fluid communication with the inlet pipe 22, such that the fluid flowing through the irrigation pipe also flows through the latching valve 52. In at least one alternate embodiment, the pre-defined threshold for the fluid pressure is set by a pressure regulator 54 in fluid communication with each of the hydraulic return actuator 48 and latching valve 52. In at least one alternate such embodiment (as illustrated in FIG. 13), the pressure regulator 54 is positioned in serial fluid communication between the hydraulic return actuator 48 and the outlet pipe 24. In such embodiments, upon the fluid pressure exceeding the pre-defined threshold, the pressure regulator 54 opens to cause the hydraulic return actuator 48 to move the main valve 36 into the closed position (or at least a partially closed position). In at least one further such alternate embodiment (as illustrated in FIGS. 14 and 15), the pressure regulator 54 is positioned in serial fluid communication between the inlet pipe 22 and the actuator valves 38 for preventing the fluid pressure within the fluid control valve 32 from exceeding a pre-defined threshold. Accordingly, in at least one such embodiment, the fluid control valve 32 is able to utilize ultra-low power micro-solenoid valves for the actuator valves 38, thereby further reducing the power consumption (and, in turn, the operational costs) of the system 20. In at least one further alternate embodiment, the at least one fluid control valve 32 does not provide for pressure regulation, and instead the first one of the actuator valves 38 is a latching solenoid valve configured for maintaining the main valve 36 in the open position without requiring any power to keep fluid pressure on an inlet side of the hydraulic actuator 34.

Figure 10:
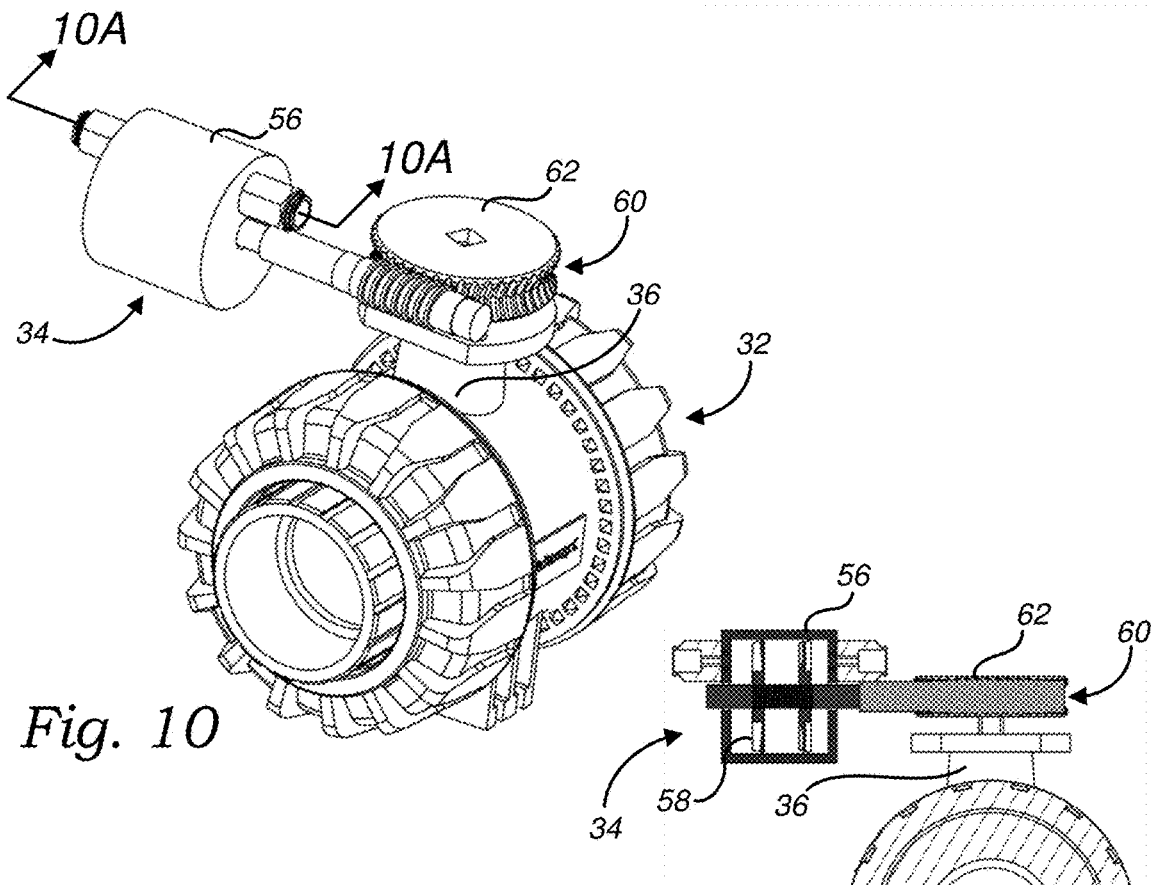
FIG. 10 is a perspective view of a still further exemplary fluid control valve, in accordance with at least one embodiment.
Figure 10A:
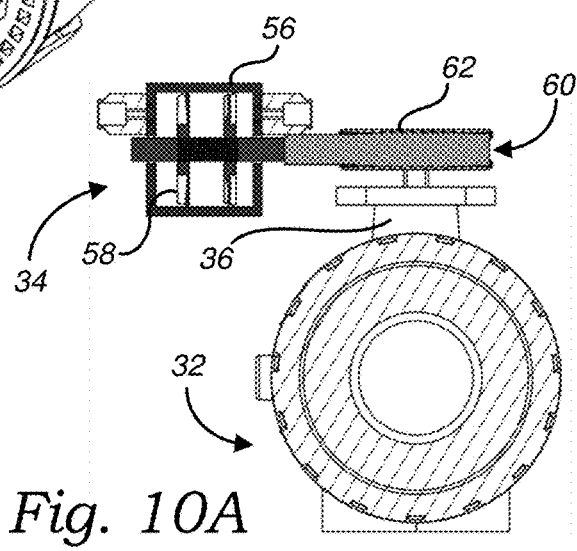
FIG. 10A is a cross-sectional view taken along line 10A-10A in FIG. 10.

In at least one alternate embodiment, as illustrated in FIGS. 10 and 10A, the hydraulic actuator 34 is a bi-directional hydraulic turbine 56 in mechanical communication with the main valve 36. In at least one such embodiment, the hydraulic turbine 56 is also in serial fluid communication between the actuator valves 38, such that the actuator valves 38 are configured for controlling the flow and direction of fluid through the hydraulic turbine 56 which, in turn, moves the hydraulic actuator 34 between the open and closed positions. In at least one embodiment, the hydraulic turbine 56 provides an at least one blade set or paddle set (hereinafter referred to generally as a "blade set" 58 for simplicity purposes) configured for rotating in each of a clockwise and counterclockwise direction depending on a direction of flow of the fluid moving therethrough. In at least one embodiment, the hydraulic turbine 56 is in mechanical communication with an at least one actuation gear 60, with the at least one actuation gear 60 being in mechanical communication with the main valve 36. Thus, in such embodiments, as the hydraulic turbine 56 rotates in the direction of the open position, the at least one actuation gear 60 is driven by the hydraulic turbine 56 to rotate the main valve 36 into the open position; and as the hydraulic turbine 56 rotates in the direction of the closed position, the at least one actuation gear 60 is driven by the hydraulic turbine 56 to rotate the main valve 36 into the closed position. In at least one embodiment, the at least one actuation gear 60 is a worm gear 62. However, in further embodiments, the at least one actuation gear 60 may be any other type of gear (or plurality of gear stages), now known or later developed, capable of functioning as described herein. In at least one alternate embodiment, the hydraulic return actuator 48 may also be a hydraulic turbine 56, similar to the hydraulic actuator 34 discussed in detail above.

Figure 16:
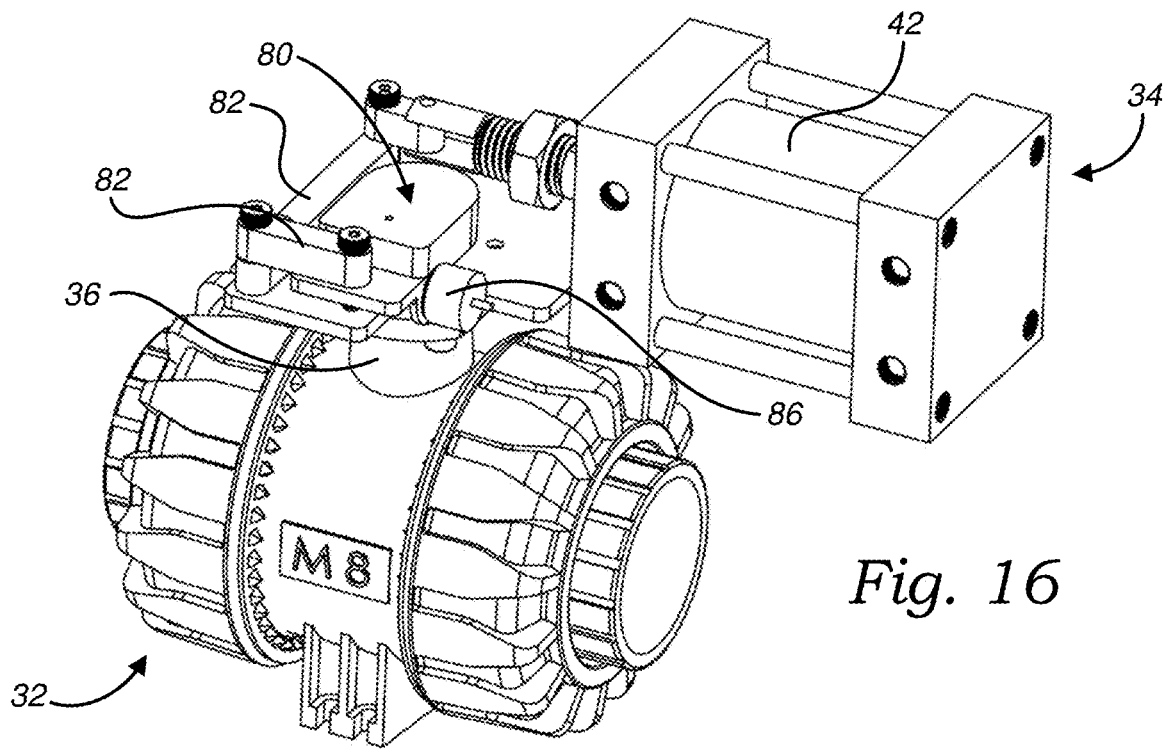
FIG. 16 is a perspective view of a still further exemplary fluid control valve, in accordance with at least one embodiment.
Figure 17:
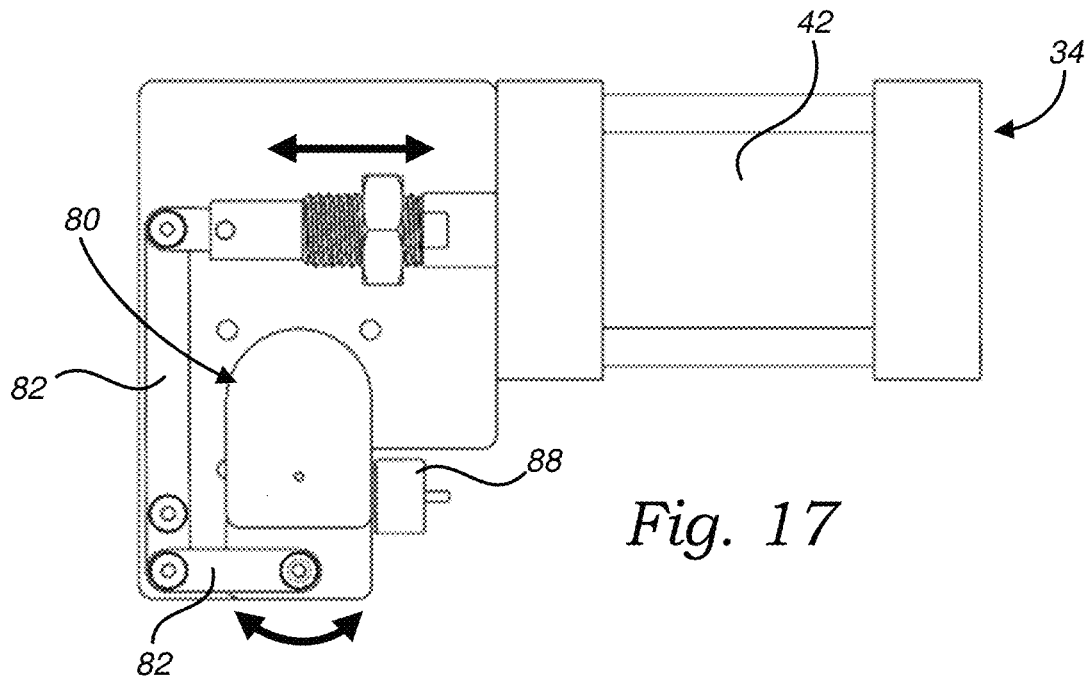
FIGS. 17 and 18 are top plan views of a hydraulic actuator of FIG. 16.
Figure 18:
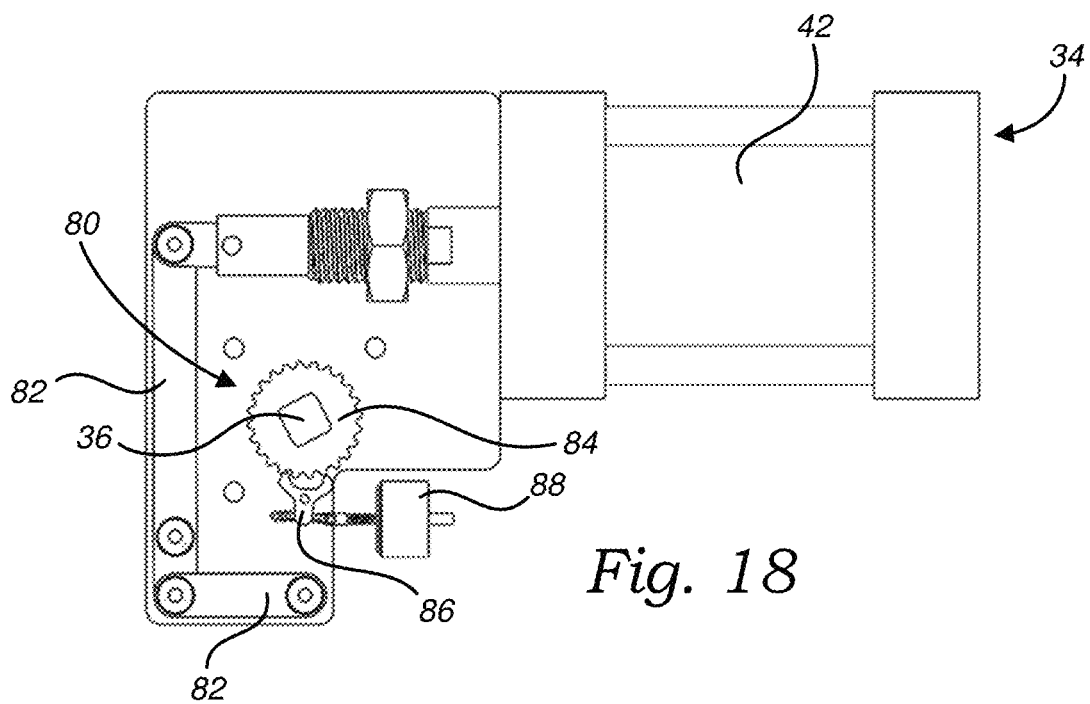

In at least one further alternate embodiment, as illustrated in FIGS. 16-18, the hydraulic actuator 34 provides a hydraulic cylinder 42 in mechanical communication with a bi-directional ratchet mechanism 80, with the ratchet mechanism 80, in turn, being in mechanical communication with the main valve 36. Thus, in such embodiments, the ratchet mechanism 80 allows the hydraulic actuator 34—through successive cycles of the hydraulic actuator 34 moving between the open and closed positions—to incrementally move the main valve 36 from the closed position to the open position (such as in 5-degree increments, for example, rather than a full 90-degree rotation of the main valve 36), and subsequently from the open position back to the closed position, which further reduces stress on the system 20, as well as the associated irrigation pipe, from any water hammer. In at least one embodiment, the hydraulic actuator 34 comprises a double acting cylinder. In at least one alternate embodiment, the hydraulic actuator 34 comprises a single acting cylinder with a return spring. In at least one embodiment, the hydraulic actuator 34 provides an at least one lever arm 82 positioned between the hydraulic cylinder 42 and the ratchet mechanism 80 for assisting with converting the linear motion of the hydraulic cylinder 42 (as the hydraulic cylinder 34 moves through successive cycles between the open and closed positions) to a rotational motion necessary for rotating the ratchet mechanism 80 relative to the main valve 36. In that regard, it should be noted that the specific sizes, shapes, dimensions, quantities and relative positions of the at least one lever arm 82 depicted in the drawings is merely exemplary and shown for illustrative purposes. Thus, in further such embodiments, the at least one lever arm 82 may take on any other sizes, shapes, dimensions, quantities and/or relative positions now known or later developed, so long as the system 20 is capable of substantially carrying out the functionality described herein.

In at least one embodiment, as best illustrated in FIG. 18, the ratchet mechanism 80 provides a ratchet gear 84 in mechanical communication with the main valve 36, a bi-directional pawl 86 selectively engageable with the ratchet gear 84 so as to limit a direction of rotation of the ratchet gear 84 relative to the main valve 36 to a single direction at any given time, and a ratchet switch 88 in mechanical communication with the pawl 86 and configured for moving the pawl 86 between a first pawl position—wherein the ratchet gear 84 is capable of rotating in a clockwise direction—and a second pawl position—wherein the ratchet gear 84 is capable of rotating in a counterclockwise direction. In at least one such embodiment, the ratchet switch 88 is a solenoid. However, in further embodiments, the ratchet switch 88 may be any other mechanism, now known or later developed, capable of moving the pawl 86 between the first and second pawl positions. It should also be noted that while the ratchet gear 84 is depicted in the drawings as being a 24-tooth gear, in further embodiments, the ratchet gear 84 may take on any other size and/or number of teeth, now known or later developed, so long as the system 20 is capable of substantially carrying out the functionality described herein. In at least one embodiment, the hydraulic actuator 34 provides a valve sensor (not shown)—such as an encoder, for example—positioned and configured for determining whether the main valve 36 is in the open position or the closed position (or partially open position, in at least one embodiment) at any given time, thereby minimizing the need for a separate sensor on the ratchet mechanism 80 itself. In at least one such embodiment, the valve sensor is capable of revealing the current direction of rotation of the ratchet mechanism 80, such that a failure of the ratchet switch 88 can be easily determined by firmware. In at least one such embodiment, the electrical power required to drive such a bi-directional ratcheting hydraulic actuator 34 is approximately 10 watts of electricity. Furthermore, given that scaling to relatively larger torques only requires a relatively larger hydraulic cylinder 42 or a ratchet gear 84 with more teeth (and, thus, a shorter angular rotation), such larger torque embodiments will not require any additional power to operate.

In still further alternate embodiments, any other hydraulic driven mechanism (or combination of mechanisms), now known or later developed, capable of being driven by the fluid flowing through the irrigation pipe, may be substituted for one or both of the hydraulic actuator 34 or the hydraulic return actuator 48, so long as the system 20 is capable of substantially carrying out the functionality described herein.

In at least one embodiment, as illustrated in FIG. 1, the system 20 also provides an at least one controller 64 positioned and configured for being in communication with each of the at least one fluid sensor 26, valve sensor (in applicable embodiments), supplemental sensor, and fluid control valve 32. Accordingly, the at least one controller 64 is configured for receiving data collected by each of the at least one fluid sensor 26, valve sensor (in applicable embodiments) and supplemental sensor, and also selectively actuating the at least one fluid control valve 32, as discussed further below. Thus, in at least one embodiment, the at least one controller 64 is configured for monitoring the position of the fluid control valve 32 (i.e., open or closed), monitoring the flow of fluid within the irrigation pipe (such as pressure and flow rate), and actuating the fluid control valve 32 as needed. In at least one embodiment, the at least one controller 64 and fluid control valve 32 are manufactured as a single unit. In at least one alternate embodiment, the at least one fluid control valve 32 is remote from the controller 64, thereby enabling the at least one controller 64 (in at least one embodiment) to selectively actuate more than one fluid control valve 32. In at least one embodiment, the at least one controller 64 provides at least one of a display screen, at least one indicator light, at least one button or keypad, and a speaker (or buzzer). Additionally, in at least one embodiment, the at least one controller 64 is in selective communication with an at least one printer.

In at least one embodiment, the system 20 also provides an at least one power supply (not shown) in electrical communication with at least one of the at least one fluid sensor 26, supplemental sensor, fluid control valve 32, and controller 64. In at least one embodiment, the at least one power supply utilizes an at least one rechargeable battery. In at least one embodiment, the at least one power supply is configured for utilizing solar power (such as via solar panels, for example), fluid power (such as via a fluid flow generator positioned within the irrigation pipe, for example), and/or wind power (such via a wind turbine, for example). In further embodiments, the at least one power supply may utilize any other form of energy (alone or in combination), now known or later developed. In this way, the system 20 is capable of operating in connection with a remotely located irrigation pipe, even where the irrigation pipe is off the grid. Given that the at least one fluid control valve 32 only requires a few watts of electricity to move between the open and closed positions, and requires no additional power to maintain the fluid control valve 32 in a given position (open, closed or even partially open) as discussed above, the amount of electricity needed to power the system 20 is relatively minimal.

It should also be noted that communication between each of the at least one fluid sensor 26, at least one supplemental sensor, at least one fluid control valve 32, and at least one controller 64 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes.

In at least one embodiment, given that the at least one fluid control valve 32 requires stored energy in the high-pressure irrigation pipe in order to be selectively actuated, steps must be taken in order to initialize the at least one fluid control valve 32 when the fluid pump of the associated irrigation pipe is primed. In at least one embodiment, after the system 20 has been installed in-line in the irrigation pipe, the controller 64 begins to actuate the main valve 36 of the at least one fluid control valve 32 into the open position (by opening the appropriate one of the actuator valves 38), and then the fluid pump associated with the irrigation pipe is turned on. To ensure that neither the irrigation pipe nor the system 20 are stressed by the pressure, the controller 64 monitors the pressure and flow rate in order to keep track of the fluid pump status. If the pressure spikes and/or the flow rate declines to near zero, the controller 64 shuts off the fluid pump; and when the pressure subsequently declines, the controller 64 turns the fluid pump back on. Once the controller 64 determines that the main valve 36 of the at least one fluid control valve 32 has fully opened, the controller 64 continues to monitor the pressure and flow rate so as to turn off the fluid pump if the pressure spikes or the flow rate declines at any point. In at least one further embodiment, the system 20 further comprises an at least one over pressure relief valve (not shown) positioned and configured for venting the fluid if the pressure within the system 20 exceeds a pre-defined threshold.

Figure 11:
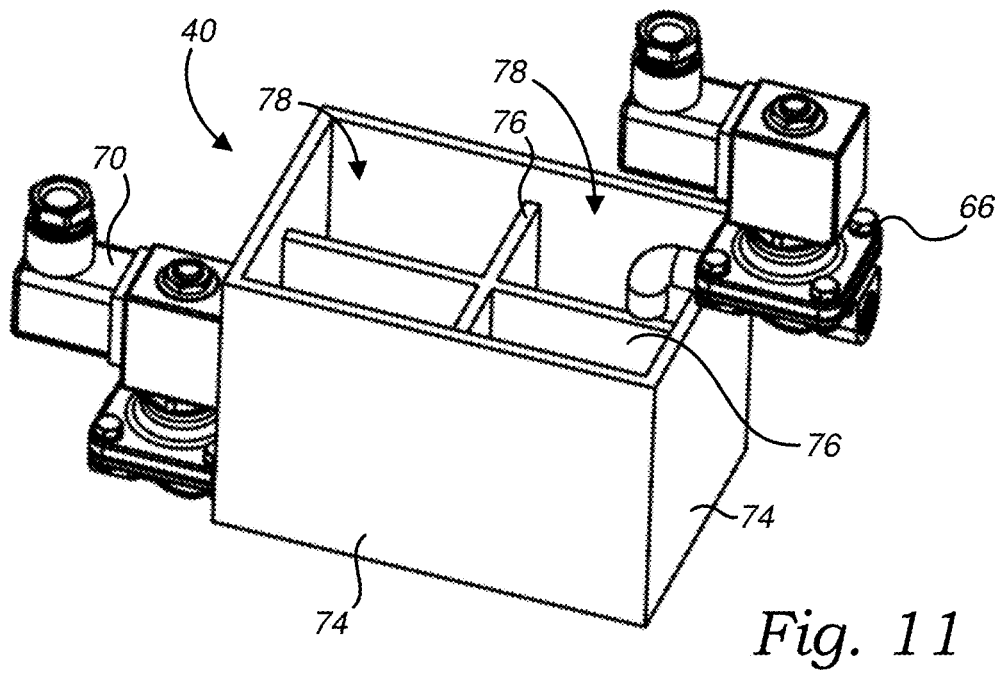
FIGS. 11 and 12 are perspective views of an exemplary sample collection tank, in accordance with at least one embodiment.
Figure 12:
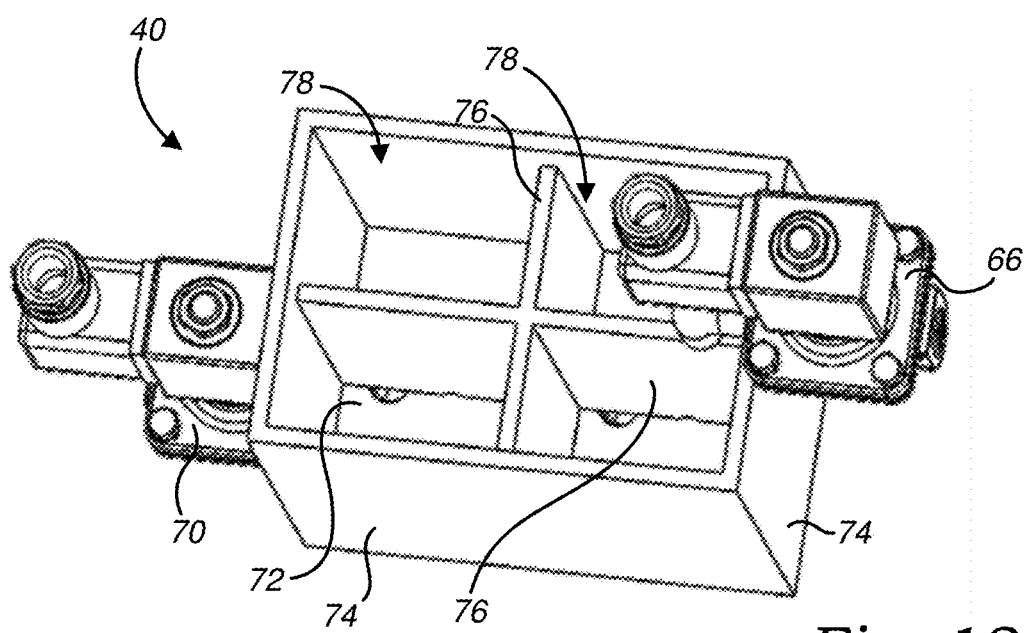

In at least one embodiment, as illustrated in FIGS. 11 and 12, the system 20 further provides an at least one sample collection tank 40 in fluid communication with at least one of the inlet pipe 22 and outlet pipe 24, and configured for temporarily storing a volume of fluid diverted from the irrigation pipe in order to be tested. In at least one embodiment, a diverter valve 66 is positioned in fluid communication between the at least one sample collection tank 40 and at least one of the inlet pipe 22 and outlet pipe 24. In at least one alternate embodiment, the diverter valve 66 and one or both of the actuator valves 38 are one and the same, such that fluid from the actuator valves 38 may be drained into the at least one sample collection tank 40 for subsequent fluid quality testing. The diverter valve 66 is configured for moving between an open position (whereby fluid is allowed to flow therethrough, into the sample collection tank 40), and a closed position (whereby fluid is prevented from flowing therethrough). In at least one embodiment, the diverter valve 66 is actuated manually. In at least one further embodiment, the diverter valve 66 is capable of being actuated automatically via the controller 64, in which case the controller 64 may be configured for periodically actuating the diverter valve 66 based on a schedule. In at least one such embodiment, the diverter valve 66 is a fluid control valve 32, similar to the embodiments discussed in detail above. In at least one embodiment, a top surface 68 of the sample collection tank 40 is removable, thereby allowing a volume of alternative fluid (i.e., fluid not directly from the irrigation pipe, such as run-off water, for example) to be manually poured into the sample collection tank 40 for testing.

In at least one embodiment, the at least one sample collection tank 40 further provides an at least one drain valve 70 positioned and configured for draining any stored fluid from the sample collection tank 40. In at least one embodiment, the drain valve 70 is actuated manually. In at least one further embodiment, the drain valve 70 is capable of being actuated automatically via the controller 64. In at least one such embodiment, the drain valve 70 is a fluid control valve 32, similar to the embodiments discussed in detail above. Additionally, in at least one embodiment, the at least one drain valve 70 is positioned and configured for draining a volume of the stored fluid into an at least one sample collection vial (not shown), thereby allowing said volume of fluid to be subsequently re-tested using alternative equipment (such as lab equipment, for example). In at least one alternate embodiment, the at least one drain valve 70 is positioned and configured for draining the stored fluid to the ground or a drain pipe. Additionally, in at least one embodiment, the controller 64 is configured for actuating each of the at least one diverter valve 66 and drain valve 70 multiple times between testing so as to flush the sample collection tank 40 before a new volume of fluid is tested.

In at least one embodiment, the at least one sample collection tank 40 provides one or more of the fluid sensors 26 installed therewithin so as to enable the system 20 to collect desired data associated with the fluid flowing through the irrigation pipe. In at least one such embodiment, one or more of the fluid sensors 26 are positioned within the sample collection tank 40 and mounted on at least one of a bottom surface 72, the top surface 68 or a side wall 74 of the sample collection tank 40. Thus, in such embodiments, the sample collection tank 40 provides a protected environment for the fluid sensors 26, where minimal algae or other biological growth can occur, given that the fluid sensors 26 would only be in contact with fluid during testing. Additionally, because the fluid sensors 26 are positioned on and/or within the sample collection tank 40, away from the high-pressure fluid flow from the irrigation pipe, the system 20 is able to utilize standard, off-the-shelf sensors, thereby further minimizing operational costs.

In at least one embodiment, as illustrated in FIGS. 11 and 12, where the fluid sensors 26 could potentially interfere with one another within the sample collection tank 40, the sample collection tank 40 provides an at least one tank partition 76 positioned and configured for creating a plurality of subcompartments 78 within the sample collection tank 40 so as to provide a sufficient amount of separation between said fluid sensors 26. In at least one embodiment, the at least one tank partition 76 is constructed out of, or otherwise coated with, a non-conductive material, so as to provide an amount of electrical isolation between one or more of the fluid sensors 26. Additionally, in at least one embodiment, the controller 64 is configured for activating less than all of the fluid sensors 26 at once (for example, activating the fluid sensors 26 one at a time), so as to reduce potential inter-sensor interference. In at least one embodiment, the at least one tank partition 76 is spaced a distance apart from at least one of the bottom surface 72, top surface 68 or side walls 74 of the sample collection tank 40, such that the subcompartments 78 are in fluid communication with one another. Thus, in at least one such embodiment, one or more of the subcompartments 78 are capable of receiving fluid from the same diverter valve 66, and are also capable of subsequently draining fluid through the same drain valve 70.

In at least one embodiment, the system 20 provides a pressurized fertilizer holding tank (not shown) in fluid communication with at least one of the inlet pipe 22 and outlet pipe 24, and configured for temporarily storing a volume of a fertilizer slurry and a volume of fluid diverted from the irrigation pipe. In at least one embodiment, the volume of fluid is used to pressurize the fertilizer holding tank. In at least one such embodiment, during operation of the system 20, the main valve 36 is partially closed in order to reduce the water pressure in the irrigation pipe downstream of the system 20 to a pressure that is less than the water pressure within the fertilizer holding tank, while the at least one fluid sensor 26 monitors the amount of fertilizer slurry that flows from the fertilizer holding tank into the irrigation pipe downstream of the system 20. An inlet solenoid valve is positioned and configured for controlling the fertilizer addition, while an outlet solenoid valve is configured for providing better control with a positive on/off and allows venting of the fertilizer holding tank when the fertilizer holding tank is refilled. In at least one embodiment, the fertilizer holding tank provides one or more sensors configured for monitoring the fertilizer output to determine when the fertilizer holding tank needs to be refilled. In at least one embodiment, because the fertilizer slurry is relatively less dense than the volume of water also occupying the fertilizer holding tank, the fertilizer slurry will float to the top of the fertilizer holding tank. In at least one further embodiment, the volume of water within the fertilizer holding tank is contained within a bladder so as to fully separate the volume of water from the volume of fertilizer slurry. In at least one such embodiment, the inlet solenoid valve is a three-way valve configured for selectively deflating the bladder to allow for the refilling of the fertilizer holding tank with a further volume of fertilizer slurry. In at least one such embodiment, the inlet solenoid valve is further configured for detecting when the bladder is fully inflated and has stopped delivering fertilizer.

Aspects of the present specification may also be described as the following embodiments:

1. An irrigation management system positionable in-line with an irrigation pipe for monitoring and controlling a flow of fluid therethrough, the system comprising: an inlet pipe and an opposing outlet pipe in serial fluid communication with the irrigation pipe; an at least one fluid control valve in serial fluid communication between the inlet pipe and outlet pipe for selectively controlling the flow of fluid therebetween, the at least one fluid control valve comprising: a main valve configured for moving between an open position—wherein fluid is able to flow from the inlet pipe, through the fluid control valve, and into the outlet pipe—and a closed position—wherein fluid is prevented from flowing into the outlet pipe; a hydraulic actuator in mechanical communication with the main valve for selectively moving the main valve between the open and closed positions; and the hydraulic actuator in serial fluid communication between a pair of actuator valves configured for moving the hydraulic actuator between an open position—wherein the hydraulic actuator moves the main valve into the open position—and a closed position—wherein the hydraulic actuator moves the main valve into the closed position; an at least one sample collection tank configured for temporarily storing a volume of fluid diverted from the irrigation pipe in order to be tested, the at least one sample collection tank comprising: a diverter valve positioned in fluid communication between the sample collection tank and at least one of the inlet pipe and outlet pipe, the diverter valve configured for moving between an open position—wherein fluid is allowed to flow therethrough, into the sample collection tank—and a closed position—wherein fluid is prevented from flowing therethrough; an at least one drain valve positioned and configured for draining any stored fluid from the sample collection tank; and an at least one fluid sensor positioned and configured for monitoring the fluid flowing through the irrigation pipe; and an at least one controller in communication with the at least one fluid sensor and fluid control valve, the at least one controller configured for receiving data collected by the at least one fluid sensor and selectively actuating the at least one fluid control valve.

2. The irrigation management system according to embodiment 1, wherein the at least one fluid sensor is at least one of a fluid flow sensor, a fluid pressure sensor, and a chemical analysis sensor.

3. The irrigation management system according to embodiments 1-2, further comprising an at least one supplemental sensor positioned and configured for gathering additional data related to the fluid flowing through the irrigation pipe and transmitting said data to the at least one controller.

4. The irrigation management system according to embodiments 1-3, wherein the at least one supplemental sensor is at least one of a fluid level sensor, a luminosity sensor, a humidity sensor, an air temperature sensor, a rain sensor, and a soil moisture sensor.

5. The irrigation management system according to embodiments 1-4, wherein the at least one supplemental sensor is at least one of an electrical current sensor and a voltage sensor positioned and configured for monitoring an electrical usage of a fluid pump in fluid communication with the irrigation pipe.

6. The irrigation management system according to embodiments 1-5, wherein the main valve of the at least one fluid control valve is at least one of a ball valve and a butterfly valve.

7. The irrigation management system according to embodiments 1-6, wherein each of the actuator valves is a 3-way solenoid valve.

8. The irrigation management system according to embodiments 1-7, wherein the actuator valves are in parallel fluid communication with the inlet pipe, such that the fluid flowing through the irrigation pipe also flows through the actuator valves and, in turn, the hydraulic actuator.

9. The irrigation management system according to embodiments 1-8, wherein a first one of the actuator valves is positioned and configured for moving the hydraulic actuator into the open position, while a second one of the actuator valves is positioned and configured for moving the hydraulic actuator into the closed position.

10. The irrigation management system according to embodiments 1-9, wherein: the hydraulic actuator is a hydraulic cylinder in mechanical communication with an actuation arm provided by the main valve; whereby, as the hydraulic actuator is moved into the open position, the hydraulic cylinder causes the actuation arm to pivot which, in turn, rotates the main valve into the open position; and whereby, as the hydraulic actuator is moved into the closed position, the hydraulic cylinder causes the actuation arm to pivot which, in turn, rotates the main valve back into the closed position.

11. The irrigation management system according to embodiments 1-10, wherein the hydraulic cylinder provides a self-lubricating dry seal between a piston and a cylinder of the hydraulic cylinder.

12. The irrigation management system according to embodiments 1-11, wherein the hydraulic cylinder comprises a double acting cylinder.

13. The irrigation management system according to embodiments 1-12, wherein the at least one fluid control valve further provides a retention spring engaged with the actuation arm and configured for increasing the force necessary for the hydraulic actuator to move the main valve out of each of the open and closed positions.

14. The irrigation management system according to embodiments 1-13, wherein the at least one fluid control valve further provides a hydraulic return actuator in mechanical communication with the main valve for moving the main valve toward the closed position upon a fluid pressure within said fluid control valve exceeding a pre-defined threshold.

15. The irrigation management system according to embodiments 1-14, wherein the hydraulic return actuator is a hydraulic cylinder, the hydraulic return actuator having a diameter that is relatively smaller than a diameter of the hydraulic actuator, thereby allowing the hydraulic return actuator to be back driven by the hydraulic actuator.

16. The irrigation management system according to embodiments 1-15, wherein the pre-defined threshold for the fluid pressure is set by a force adjustable spring positioned on the hydraulic return actuator, the spring configured for biasing the main valve into the open position.

17. The irrigation management system according to embodiments 1-16, wherein the at least one fluid control valve further provides a latching valve positioned and configured for maintaining the main valve in the closed position after the main valve has been moved into the closed position by the hydraulic return actuator.

18. The irrigation management system according to embodiments 1-17, wherein the pre-defined threshold for the fluid pressure is set by a pressure regulator in fluid communication with each of the hydraulic return actuator and latching valve, the pressure regulator configured for opening upon the fluid pressure exceeding the pre-defined threshold, thereby causing the hydraulic return actuator to move the main valve into the closed position.

19. The irrigation management system according to embodiments 1-18, wherein the latching valve is in parallel fluid communication with the inlet pipe, such that the fluid flowing through the irrigation pipe also flows through the latching valve.

20. The irrigation management system according to embodiments 1-19, wherein the latching valve is a 3-way latching solenoid valve.

21. The irrigation management system according to embodiments 1-20, wherein:
the main valve is in mechanical communication with an at least one actuation gear; and the hydraulic actuator is a bi-directional hydraulic turbine in mechanical communication with the at least one actuation gear, the hydraulic turbine providing an at least one blade set configured for rotating in each of a clockwise and counterclockwise direction, depending on a direction of flow of the fluid moving therethrough via the actuator valves, which, in turn, drives the at least one actuation gear to rotate the main valve between the open and closed positions.

22. The irrigation management system according to embodiments 1-21, wherein the at least one actuation gear is a worm gear.

23. The irrigation management system according to embodiments 1-22, wherein the hydraulic return actuator is a bi-directional hydraulic turbine.

24. The irrigation management system according to embodiments 1-23, wherein: the hydraulic actuator comprises: a bi-directional ratchet mechanism in mechanical communication with the main valve, the ratchet mechanism comprising: a ratchet gear in mechanical communication with the main valve; a bi-directional pawl selectively engageable with the ratchet gear; and a ratchet switch in mechanical communication with the pawl and configured for moving the pawl between a first pawl position—wherein the ratchet gear is permitted to rotate in a first rotational direction—and a second pawl position—wherein the ratchet gear is permitted to rotate in an opposing second rotational direction; and a hydraulic cylinder in mechanical communication with the ratchet gear; whereby, with the pawl in the first pawl position, successive linear movements of the hydraulic cylinder cause the ratchet gear to rotate in the first rotational direction which, in turn, causes the main valve to incrementally move into the open position; and whereby, with the pawl in the second pawl position, successive linear movements of the hydraulic cylinder cause the ratchet gear to rotate in the second rotational direction which, in turn, causes the main valve to incrementally move into the closed position.

25. The irrigation management system according to embodiments 1-24, wherein the hydraulic cylinder is a double acting cylinder.

26. The irrigation management system according to embodiments 1-25, the hydraulic cylinder is a single acting cylinder with a return spring.

27. The irrigation management system according to embodiments 1-26, wherein the hydraulic actuator further comprises an at least one lever arm positioned in mechanical communication between the hydraulic cylinder and the ratchet gear.

28. The irrigation management system according to embodiments 1-27, wherein the ratchet switch is a solenoid.

29. The irrigation management system according to embodiments 1-28, further comprising an at least one power supply in electrical communication with at least one of the at least one fluid sensor, fluid control valve, and controller.

30. The irrigation management system according to embodiments 1-29, wherein the at least one power supply utilizes an at least one rechargeable battery.

31. The irrigation management system according to embodiments 1-30, wherein the at least one power supply is configured for utilizing at least one of solar power, fluid power, and wind power.

32. The irrigation management system according to embodiments 1-31, wherein the at least one controller is further in communication with the diverter valve of the at least one sample collection tank, the at least one controller configured for selectively actuating said diverter valve.

33. The irrigation management system according to embodiments 1-32, wherein the at least one controller is further in communication with the at least one drain valve of the at least one sample collection tank, the at least one controller configured for selectively actuating said at least one drain valve.

34. The irrigation management system according to embodiments 1-33, wherein the at least one sample collection tank further provides an at least one sample collection vial positioned and configured for receiving a volume of the stored fluid as it exits the at least one drain valve.

35. The irrigation management system according to embodiments 1-34, wherein the at least one fluid sensor is positioned within the at least one sample collection tank and mounted on at least one of a bottom surface, a top surface or a side wall of said sample collection tank.

36. The irrigation management system according to embodiments 1-35, wherein the at least one sample collection tank further comprises an at least one tank partition positioned and configured for creating a plurality of subcompartments within said sample collection tank.

37. The irrigation management system according to embodiments 1-36, wherein the at least one tank partition is constructed out of, or otherwise coated with, a non-conductive material.

38. The irrigation management system according to embodiments 1-37, wherein the at least one tank partition is spaced a distance apart from at least one of the bottom surface, top surface or side walls of the sample collection tank, such that the subcompartments are in fluid communication with one another.

39. A fluid control valve positionable in serial fluid communication between an inlet pipe and an outlet pipe for selectively controlling the flow of fluid therebetween, the fluid control valve comprising: a main valve configured for moving between an open position—wherein fluid is able to flow from the inlet pipe, through the fluid control valve, and into the outlet pipe—and a closed position—wherein fluid is prevented from flowing into the outlet pipe; a hydraulic actuator in mechanical communication with the main valve for selectively moving the main valve between the open and closed positions; and the hydraulic actuator in serial fluid communication between a pair of actuator valves configured for moving the hydraulic actuator between an open position—wherein the hydraulic actuator moves the main valve into the open position—and a closed position—wherein the hydraulic actuator moves the main valve into the closed position.

40. The fluid control valve according to embodiment 39, wherein the main valve is at least one of a ball valve and a butterfly valve.

41. The fluid control valve according to embodiments 39-40, wherein each of the actuator valves is a 3-way solenoid valve.

42. The fluid control valve according to embodiments 39-41, wherein the actuator valves are in parallel fluid communication with the inlet pipe, such that the fluid flowing through the inlet pipe also flows through the actuator valves and, in turn, the hydraulic actuator.

43. The fluid control valve according to embodiments 39-42, wherein a first one of the actuator valves is positioned and configured for moving the hydraulic actuator into the open position, while a second one of the actuator valves is positioned and configured for moving the hydraulic actuator into the closed position.

44. The fluid control valve according to embodiments 39-43, wherein: the hydraulic actuator is a hydraulic cylinder in mechanical communication with an actuation arm provided by the main valve; whereby, as the hydraulic actuator is moved into the open position, the hydraulic cylinder causes the actuation arm to pivot which, in turn, rotates the main valve into the open position; and whereby, as the hydraulic actuator is moved into the closed position, the hydraulic cylinder causes the actuation arm to pivot which, in turn, rotates the main valve back into the closed position.

45. The fluid control valve according to embodiments 39-44, wherein the hydraulic cylinder provides a self-lubricating dry seal between a piston and a cylinder of the hydraulic cylinder.

46. The fluid control valve according to embodiments 39-45, wherein the hydraulic cylinder comprises a double acting cylinder.

47. The fluid control valve according to embodiments 39-46, further comprising a retention spring engaged with the actuation arm and configured for increasing the force necessary for the hydraulic actuator to move the main valve out of each of the open and closed positions.

48. The fluid control valve according to embodiments 39-47, further comprising a hydraulic return actuator in mechanical communication with the main valve for moving the main valve toward the closed position upon a fluid pressure within the fluid control valve exceeding a pre-defined threshold.

49. The fluid control valve according to embodiments 39-48, wherein the hydraulic return actuator is a hydraulic cylinder, the hydraulic return actuator having a diameter that is relatively smaller than a diameter of the hydraulic actuator, thereby allowing the hydraulic return actuator to be back driven by the hydraulic actuator.

50. The fluid control valve according to embodiments 39-49, wherein the pre-defined threshold for the fluid pressure is set by a force adjustable spring positioned on the hydraulic return actuator, the spring configured for biasing the main valve into the open position.

51. The fluid control valve according to embodiments 39-50, further comprising a latching valve positioned and configured for maintaining the main valve in the closed position after the main valve has been moved into the closed position by the hydraulic return actuator.

52. The fluid control valve according to embodiments 39-51, wherein the pre-defined threshold for the fluid pressure is set by a pressure regulator in fluid communication with each of the hydraulic return actuator and latching valve, the pressure regulator configured for opening upon the fluid pressure exceeding the pre-defined threshold, thereby causing the hydraulic return actuator to move the main valve into the closed position.

53. The fluid control valve according to embodiments 39-52, wherein the latching valve is in parallel fluid communication with the inlet pipe, such that the fluid flowing through the inlet pipe also flows through the latching valve.

54. The fluid control valve according to embodiments 39-53, wherein the latching valve is a 3-way latching solenoid valve.

55. The fluid control valve according to embodiments 39-54, wherein: the main valve is in mechanical communication with an at least one actuation gear; and the hydraulic actuator is a bi-directional hydraulic turbine in mechanical communication with the at least one actuation gear, the hydraulic turbine providing an at least one blade set configured for rotating in each of a clockwise and counterclockwise direction, depending on a direction of flow of the fluid moving therethrough via the actuator valves, which, in turn, drives the at least one actuation gear to rotate the main valve between the open and closed positions.

56. The fluid control valve according to embodiments 39-55, wherein the at least one actuation gear is a worm gear.

57. The fluid control valve according to embodiments 39-56, wherein the hydraulic return actuator is a bi-directional hydraulic turbine.

58. The irrigation management system according to embodiments 39-57, wherein: the hydraulic actuator comprises: a bi-directional ratchet mechanism in mechanical communication with the main valve, the ratchet mechanism comprising: a ratchet gear in mechanical communication with the main valve; a bi-directional pawl selectively engageable with the ratchet gear; and a ratchet switch in mechanical communication with the pawl and configured for moving the pawl between a first pawl position—wherein the ratchet gear is permitted to rotate in a first rotational direction—and a second pawl position—wherein the ratchet gear is permitted to rotate in an opposing second rotational direction; and a hydraulic cylinder in mechanical communication with the ratchet gear; whereby, with the pawl in the first pawl position, successive linear movements of the hydraulic cylinder cause the ratchet gear to rotate in the first rotational direction which, in turn, causes the main valve to incrementally move into the open position; and whereby, with the pawl in the second pawl position, successive linear movements of the hydraulic cylinder cause the ratchet gear to rotate in the second rotational direction which, in turn, causes the main valve to incrementally move into the closed position.

59. The irrigation management system according to embodiments 39-58, wherein the hydraulic cylinder is a double acting cylinder.

60. The irrigation management system according to embodiments 39-59, the hydraulic cylinder is a single acting cylinder with a return spring.

61. The irrigation management system according to embodiments 39-60, wherein the hydraulic actuator further comprises an at least one lever arm positioned in mechanical communication between the hydraulic cylinder and the ratchet gear.

62. The irrigation management system according to embodiments 39-61, wherein the ratchet switch is a solenoid.

63. A sample collection tank positionable in fluid communication with an inlet pipe for temporarily storing a volume of fluid diverted from the inlet pipe in order to be tested, the at least one sample collection tank comprising: a diverter valve positioned in fluid communication between the sample collection tank and the inlet pipe, the diverter valve configured for moving between an open position—wherein fluid is allowed to flow therethrough, into the sample collection tank—and a closed position—wherein fluid is prevented from flowing therethrough; an at least one drain valve positioned and configured for draining any stored fluid from the sample collection tank; and an at least one fluid sensor positioned and configured for monitoring the fluid flowing through the inlet pipe.

64. The sample collection tank according to embodiment 63, wherein the at least one fluid sensor is at least one of a fluid flow sensor, a fluid pressure sensor, and a chemical analysis sensor.

65. The sample collection tank according to embodiments 63-64, further comprising an at least one sample collection vial positioned and configured for receiving a volume of the stored fluid as it exits the at least one drain valve.

66. The sample collection tank according to embodiments 63-65, wherein the at least one fluid sensor is positioned within the sample collection tank and mounted on at least one of a bottom surface, a top surface or a side wall of the sample collection tank.

67. The sample collection tank according to embodiments 63-66, further comprising an at least one tank partition positioned and configured for creating a plurality of subcompartments within the sample collection tank.

68. The sample collection tank according to embodiments 63-67, wherein the at least one tank partition is constructed out of, or otherwise coated with, a non-conductive material.

69. The sample collection tank according to embodiments 63-68, wherein the at least one tank partition is spaced a distance apart from at least one of the bottom surface, top surface or side walls of the sample collection tank, such that the subcompartments are in fluid communication with one another.

In closing, regarding the exemplary embodiments of the present invention as shown and described herein, it will be appreciated that an irrigation management system is disclosed that provides cost-effective, less power consuming irrigation valves, and cost-effective in-line water quality testing capabilities. Because the principles of the invention may be practiced in a number of configurations beyond those shown and described, it is to be understood that the invention is not in any way limited by the exemplary embodiments, but is generally directed to an irrigation management system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term.

Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment. Additionally, the various illustrative logical blocks, modules, methods, and algorithm processes and sequences described in connection with the embodiments disclosed herein can be implemented as electronic hardware, computer software, or combinations of both. To clearly illustrate this interchangeability of hardware and software, various illustrative components, blocks, modules, and process actions have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of this document.

The phrase "non-transitory," in addition to having its ordinary meaning, as used in this document means "enduring or long-lived". The phrase "non-transitory computer readable medium," in addition to having its ordinary meaning, includes any and all computer readable mediums, with the sole exception of a transitory, propagating signal.

This includes, by way of example and not limitation, non-transitory computer-readable mediums such as register memory, processor cache and random-access memory ("RAM").

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other inlet device, and a central processor.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An irrigation management system positionable in-line with an irrigation pipe for monitoring and controlling a flow of fluid therethrough, the system comprising:
    an inlet pipe and an opposing outlet pipe in serial fluid communication with the irrigation pipe;
    an at least one fluid control valve in serial fluid communication between the inlet pipe and outlet pipe for selectively controlling the flow of fluid therebetween, the at least one fluid control valve comprising:
        a main valve configured for moving between an open position—wherein fluid is able to flow from the inlet pipe, through the fluid control valve, and into the outlet pipe—and a closed position—wherein fluid is prevented from flowing into the outlet pipe;
        a hydraulic actuator in mechanical communication with the main valve for selectively moving the main valve between the open and closed positions; and
        the hydraulic actuator in serial fluid communication between a pair of actuator valves configured for moving the hydraulic actuator between an open position—wherein the hydraulic actuator moves the main valve into the open position—and a closed position—wherein the hydraulic actuator moves the main valve into the closed position;
    an at least one sample collection tank configured for temporarily storing a volume of fluid diverted from the irrigation pipe in order to be tested, the at least one sample collection tank comprising:
        a diverter valve positioned in fluid communication between the sample collection tank and at least one of the inlet pipe and outlet pipe, the diverter valve configured for moving between an open position—wherein fluid is allowed to flow therethrough, into the sample collection tank—and a closed position—wherein fluid is prevented from flowing therethrough;
        an at least one drain valve positioned and configured for draining any stored fluid from the sample collection tank; and
        an at least one fluid sensor positioned and configured for monitoring the fluid flowing through the irrigation pipe; and
    an at least one controller in communication with the at least one fluid sensor and fluid control valve, the at least one controller configured for receiving data collected by the at least one fluid sensor and selectively actuating the at least one fluid control valve.

2. The irrigation management system of claim 1, wherein the at least one fluid sensor is at least one of a fluid flow sensor, a fluid pressure sensor, and a chemical analysis sensor.

3. The irrigation management system of claim 1, wherein the main valve of the at least one fluid control valve is at least one of a ball valve and a butterfly valve.

4. The irrigation management system of claim 1, wherein each of the actuator valves is a 3-way solenoid valve.

5. The irrigation management system of claim 1, wherein a first one of the actuator valves is positioned and configured for moving the hydraulic actuator into the open position, while a second one of the actuator valves is positioned and configured for moving the hydraulic actuator into the closed position.

6. The irrigation management system of claim 1, wherein:
the hydraulic actuator is a hydraulic cylinder in mechanical communication with an actuation arm provided by the main valve;
whereby, as the hydraulic actuator is moved into the open position, the hydraulic cylinder causes the actuation arm to pivot which, in turn, rotates the main valve into the open position; and
whereby, as the hydraulic actuator is moved into the closed position, the hydraulic cylinder causes the actuation arm to pivot which, in turn, rotates the main valve back into the closed position.

7. The irrigation management system of claim 6, wherein the at least one fluid control valve further provides a retention spring engaged with the actuation arm and configured for increasing the force necessary for the hydraulic actuator to move the main valve out of each of the open and closed positions.

8. The irrigation management system of claim 6, wherein the at least one fluid control valve further provides a hydraulic return actuator in mechanical communication with the main valve for moving the main valve toward the closed position upon a fluid pressure within said fluid control valve exceeding a pre-defined threshold.

9. The irrigation management system of claim 8, wherein the pre-defined threshold for the fluid pressure is set by a force adjustable spring positioned on the hydraulic return actuator, the spring configured for biasing the main valve into the open position.

10. The irrigation management system of claim 6, wherein the at least one fluid control valve further provides a latching valve positioned and configured for maintaining the main valve in the closed position after the main valve has been moved into the closed position by the hydraulic return actuator.

11. The irrigation management system of claim 10, wherein the pre-defined threshold for the fluid pressure is set by a pressure regulator in fluid communication with each of the hydraulic return actuator and latching valve, the pressure regulator configured for opening upon the fluid pressure exceeding the pre-defined threshold, thereby causing the hydraulic return actuator to move the main valve into the closed position.

12. The irrigation management system of claim 1, wherein:
the hydraulic actuator comprises:
a bi-directional ratchet mechanism in mechanical communication with the main valve, the ratchet mechanism comprising:
a ratchet gear in mechanical communication with the main valve;
a bi-directional pawl selectively engageable with the ratchet gear; and
a ratchet switch in mechanical communication with the pawl and configured for moving the pawl between a first pawl position—wherein the ratchet gear is permitted to rotate in a first rotational direction—and a second pawl position—wherein the ratchet gear is permitted to rotate in an opposing second rotational direction; and
a hydraulic cylinder in mechanical communication with the ratchet gear;
whereby, with the pawl in the first pawl position, successive linear movements of the hydraulic cylinder cause the ratchet gear to rotate in the first rotational direction which, in turn, causes the main valve to incrementally move into the open position; and
whereby, with the pawl in the second pawl position, successive linear movements of the hydraulic cylinder cause the ratchet gear to rotate in the second rotational direction which, in turn, causes the main valve to incrementally move into the closed position.

13. The irrigation management system of claim 12, wherein the hydraulic actuator further comprises an at least one lever arm positioned in mechanical communication between the hydraulic cylinder and the ratchet gear.

14. The irrigation management system of claim 1, wherein the at least one sample collection tank further provides an at least one sample collection vial positioned and configured for receiving a volume of the stored fluid as it exits the at least one drain valve.

15. The irrigation management system of claim 1, wherein the at least one fluid sensor is positioned within the at least one sample collection tank and mounted on at least one of a bottom surface, a top surface or a side wall of said sample collection tank.

16. The irrigation management system of claim 1, wherein the at least one sample collection tank further comprises an at least one tank partition positioned and configured for creating a plurality of subcompartments within said sample collection tank.

17. The irrigation management system of claim 16, wherein the at least one tank partition is constructed out of, or otherwise coated with, a non-conductive material.

18. The irrigation management system of claim 16, wherein the at least one tank partition is spaced a distance apart from at least one of the bottom surface, top surface or side walls of the sample collection tank, such that the subcompartments are in fluid communication with one another.

19. A fluid control valve positionable in serial fluid communication between an inlet pipe and an outlet pipe for selectively controlling the flow of fluid therebetween, the fluid control valve comprising:
a main valve configured for moving between an open position—wherein fluid is able to flow from the inlet pipe, through the fluid control valve, and into the outlet pipe—and a closed position—wherein fluid is prevented from flowing into the outlet pipe;
a hydraulic actuator in mechanical communication with the main valve for selectively moving the main valve between the open and closed positions; and
the hydraulic actuator in serial fluid communication between a pair of actuator valves configured for moving the hydraulic actuator between an open position—wherein the hydraulic actuator moves the main valve into the open position—and a closed position—wherein the hydraulic actuator moves the main valve into the closed position.

20. A sample collection tank positionable in fluid communication with an inlet pipe for temporarily storing a volume of fluid diverted from the inlet pipe in order to be tested, the at least one sample collection tank comprising:
a diverter valve positioned in fluid communication between the sample collection tank and the inlet pipe, the diverter valve configured for moving between an open position—wherein fluid is allowed to flow therethrough, into the sample collection tank—and a closed position—wherein fluid is prevented from flowing therethrough;

an at least one drain valve positioned and configured for draining any stored fluid from the sample collection tank; and an at least one fluid sensor positioned and configured for monitoring the fluid flowing through the inlet pipe.

* * * * *